(12) United States Patent
Isaacson (10) Patent No.: US 10,940,305 B2
(45) Date of Patent: Mar. 9, 2021

(54) SMART SMALL-BORE CONNECTOR DEVICE

(71) Applicant: Becton, Dickinson and Company, Franklin Lakes, NJ (US)

(72) Inventor: S. Ray Isaacson, Layton, UT (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 212 days.

(21) Appl. No.: 16/108,974

(22) Filed: Aug. 22, 2018

(65) Prior Publication Data
US 2019/0070402 A1 Mar. 7, 2019

Related U.S. Application Data

(60) Provisional application No. 62/554,905, filed on Sep. 6, 2017.

(51) Int. Cl.
*A61M 39/00* (2006.01)
*A61M 39/10* (2006.01)
*A61M 39/12* (2006.01)
*A61M 25/00* (2006.01)

(52) U.S. Cl.
CPC ........ *A61M 39/1011* (2013.01); *A61M 39/10* (2013.01); *A61M 39/12* (2013.01); *A61M 25/0014* (2013.01); *A61M 25/0097* (2013.01); *A61M 2039/1022* (2013.01); *A61M 2039/1083* (2013.01)

(58) Field of Classification Search
CPC ...... A61M 2039/1022; A61M 25/0014; A61M 25/0097
See application file for complete search history.

(56) References Cited

U.S. PATENT DOCUMENTS

| | | | | |
|---|---|---|---|---|
| 4,362,166 A * | 12/1982 | Furler | ................ | A61B 5/02055 |
| | | | | 439/278 |
| 5,722,960 A * | 3/1998 | Duplan | ................ | A61M 5/322 |
| | | | | 604/110 |
| 5,947,911 A * | 9/1999 | Wong | ................ | A61B 5/14557 |
| | | | | 600/309 |
| 6,717,501 B2 * | 4/2004 | Hall | ................ | H01R 13/533 |
| | | | | 336/132 |
| 8,412,329 B2 * | 4/2013 | Mokelke | ................ | A61N 1/056 |
| | | | | 607/37 |

(Continued)

FOREIGN PATENT DOCUMENTS

CN 101854853 10/2010
WO 2009/003138 12/2008

*Primary Examiner* — William R Carpenter
(74) *Attorney, Agent, or Firm* — Kirton & McConkie; Craig Metcalf; Kevin Stinger (57) ABSTRACT

A connector device includes a connector. An electrical lead wire is positioned in the connector. The electrical lead wire is configured to provide communication between the connector device and an external device. In certain embodiments, the electrical lead wire includes a contact point on a surface of the connector for electrically coupling the connector device to the external device. In addition to or as an alternative to the electrical lead wire, the connector device may include an optical coupling or channel in the connector configured for optical light transmission between the connector device and the external device.

20 Claims, 3 Drawing Sheets

(56) References Cited

U.S. PATENT DOCUMENTS

| | | | | |
|---|---|---|---|---|
| 2008/0200789 A1* | 8/2008 | Brister | ............... | A61B 5/14532 |
| | | | | 600/347 |
| 2008/0265191 A1* | 10/2008 | Walborn | ............... | A61M 39/22 |
| | | | | 251/129.01 |
| 2009/0270941 A1* | 10/2009 | Mokelke | ........... | A61M 39/0606 |
| | | | | 607/37 |
| 2011/0009817 A1* | 1/2011 | Bennett | .................. | G01N 21/17 |
| | | | | 604/93.01 |
| 2013/0345587 A1* | 12/2013 | Colman | ................ | F16L 37/244 |
| | | | | 600/532 |
| 2015/0306365 A1* | 10/2015 | Besko | ................ | H01R 13/6616 |
| | | | | 604/111 |
| 2016/0193453 A1* | 7/2016 | Isaacson | ........... | A61M 25/0097 |
| | | | | 604/263 |

\* cited by examiner

SMART SMALL-BORE CONNECTOR DEVICE

CROSS-REFERENCE TO RELATED APPLICATION

This application claims the benefit of U.S. Provisional Application No. 62/554,905, entitled "Smart Small-Bore Connector Device," filed Sep. 6, 2017, which is hereby incorporated by reference in its entirety.

TECHNICAL FIELD

The present disclosure is directed to small-bore connector devices for liquids and gases. More specifically, the present disclosure is directed to smart small-bore devices for healthcare applications having a fitting or connection that includes one or more electrical lead wires and one or more corresponding electrical contacts to electrically couple the smart small-bore connector device with an external device, such as a delivery device and/or a monitoring device.

BACKGROUND

Luer fittings or connections are used extensively in medical and life sciences applications. Conventional Luer fittings are typically small-bore, leak-proof couplings used to couple tubing and equipment for the transfer of fluids and gases, for example.

Conventional Luer fittings include slip Luer fittings and Luer lock fittings. The specifications and performance of these fittings are covered by International Standard ISO 80369 entitled "Small-bore connectors for liquids and gases in healthcare applications." The slip Luer fittings simply conform to Luer taper dimensions and are pressed together and held by friction, and the Luer lock fittings include a twist-lock mechanism to hold a hypodermic needle safely in place, for example. The Luer lock fitting allows the needle to be coupled and removed from a syringe, minimizing a risk that the needle slips off the syringe and/or that the syringe tip breaks. The cooperating slip Luer fittings slip together to form a seal. Cooperating Luer lock fittings, on the other hand, have interlocking threads to maintain the leak-proof coupling between the needle and the syringe. One portion of the Luer lock fitting (e.g., the syringe tip) has a housing with external threads, while the cooperating portion of the Luer lock fitting (e.g., the base of the needle) has a housing with internal threads. These threads urge the two portions together to provide a leak-proof coupling that can be easily disengaged.

Luer fittings or connections are widely used in laboratories, medical devices and intervention therapies. Examples of Luer fittings include, without limitation, intravenous catheters, feeding tubes, ventilators, and the common hypodermic syringe. Luer fittings are available in a variety of materials, such as nylon, polycarbonate, polypropylene, polyether ether ketone (PEEK), and stainless steel, for example.

BRIEF SUMMARY OF SOME EXAMPLE EMBODIMENTS

In one aspect, a small-bore connector device includes a plurality of conductive elements, such as electrical lead wires, positioned in or insert molded into at least a portion of the small-bore connector device, e.g., at an adapter or base of the small-bore connector device. Each conductive element includes a contact point on a surface of the small-bore connector device and coupled to a respective electrical lead wire. For example, the contact point may be positioned on an outer surface of the base or on a surface of a flange at the proximal end of the small-bore connector device. The conductive elements may have any suitable number of contact points. The one or more electrical lead wires electrically couple, e.g., in signal communication, the small-bore connector device and, in certain embodiments, a medical device, component, or instrument operatively coupled to the small-bore connector device, to an external device, such as a monitoring device and/or delivery device.

In another aspect, a small-bore connector device includes one or more suitable optical connections, e.g., one or more optical fibers, formed or molded in the small-bore connector device for optical light transmission (fiber optic transmission) between the small-bore connector device and an external device, such as a monitoring device and/or delivery device. In certain embodiments, this feature is molded in a clear material to provide a fiber optic transmission line or cable without requiring additional parts or components. Additionally or alternatively, one or more data connections, similar to a TOS-LINK® audio transmission cable, is positioned or molded in the small-bore connector device for data transmission through the small-bore connector device.

In another aspect, a catheter assembly includes a catheter having a distal end and an opposing proximal end. A connector is coupled in fluid communication to the proximal end of the catheter. The connector includes a base including a sensor assembly having at least one sensor. The at least one sensor is configured to sense one or more environmental characteristics at an access site and generate at least one signal representative of the one or more environmental characteristics. An electrical lead wire operatively couples the at least one sensor to an external device. The electrical lead wire is configured to transmit the at least one signal received from the at least one sensor to the external device.

In another aspect, a catheter assembly includes a catheter having a distal end and an opposing proximal end, and a cannula extending from distal end toward proximal end. A connector is coupled in fluid communication with the catheter. The connector is configured to provide electrical communication between the catheter assembly and an external device. The connector includes a base having a flange forming threads. A sensor assembly is coupled to the base. The sensor assembly is configured to sense one or more environmental characteristics at an access site and generate at least one signal representative of the one or more environmental characteristics. A coupling is configured to operatively couple the connector to the external device. The coupling is configured to transmit at least one of a data signal and a command signal between the sensor assembly and the external device.

In another aspect, a connector device includes a connector configured to provide electrical communication between the connector device and an external device. The connector includes a base having a flange forming threads. A sensor is coupled to the base. The sensor is configured to sense an environmental characteristic at an access site and generate a signal representative of the environmental characteristic. A coupling is configured to operatively couple the connector to the external device. The coupling is configured to transmit a signal between the sensor and the external device.

DETAILED DESCRIPTION

Various embodiments are described below with reference to the drawings in which like elements generally are referred to by like numerals. The relationship and functioning of the various elements of the embodiments may better be understood by reference to the following detailed description. However, embodiments are not limited to those illustrated in the drawings. It should be understood that the drawings are not necessarily to scale, and in certain instances details may have been omitted that are not necessary for an understanding of embodiments disclosed herein, such as—for example—conventional fabrication and assembly.

The invention is defined by the claims, may be embodied in many different forms, and should not be construed as limited to the embodiments set forth herein; rather, these embodiments are provided so that this disclosure will be thorough and complete, and will fully convey enabling disclosure to those skilled in the art. As used in this specification and the claims, the singular forms "a," "an," and "the" include plural referents unless the context clearly dictates otherwise. Reference herein to any industry standards (e.g., ASTM, ANSI, IEEE, ISO standards) is defined as complying with the currently published standards as of the original filing date of this disclosure concerning the units, measurements, and testing criteria communicated by those standards unless expressly otherwise defined herein. The terms "proximal" and "distal" are used herein in the common usage sense where they refer respectively to a handle/doctor-end of a device or related object and a tool/patient-end of a device or related object. The terms "about," "substantially," "generally," and other terms of degree, when used with reference to any volume, dimension, proportion, or other quantitative or qualitative value, are intended to communicate a definite and identifiable value within the standard parameters that would be understood by one of skill in the art (equivalent to a medical device engineer with experience in this field), and should be interpreted to include at least any legal equivalents, minor but functionally-insignificant variants, standard manufacturing tolerances, and including at least mathematically significant figures (although not required to be as broad as the largest range thereof).

In example embodiments, previously unused space on a small-bore fitting or connection, such as a small-bore connector device, is utilized to facilitate electrical communication, e.g., power and/or signal communication, between a suitable upstream source, such as a therapy infusate source, and the small-bore fitting or connection used for any suitable type of patient access. The example small-bore connector device is suitable for use in infusion therapy, for Peripherally Inserted Central Catheter (PICC) lines, shunts, and ports, for example. The small-bore fitting or connection can be used on needleless connectors or any device that utilizes a small-bore compatible fitting or connection for fluid flow or fluid communication. The example small-bore connector devices provide a communication device that can link in a closed loop the inserted medical device with any type of delivery or information system via an electrical and data connection built into the small-bore connector device. In example embodiments, the small-bore fittings or connections include communication devices in the defined space of the small-bore fitting or connection to provide power and/or data transmission into and/or out of the connection through the small-bore fitting or connection, and feedback from the distal side back to the proximal side. The example small-bore connectors described herein satisfy the requirements of International Standards ISO 80369 for passage of liquids and gases in healthcare applications and provide improvements or enhancements to add advanced functionality to the standard small-bore connectors satisfying the requirements of ISO 80369. In alternative embodiments, the example small-bore connector device may be suitable for other applications not associated with ISO 80369.

A smart small-bore connector device, as described herein, provides electrical communication, e.g., power and/or signal communication, between a medical device or instrument at a distal end of the smart small-bore connector device and an external device, such as a fluid or medication delivery device and/or a monitoring device, at an opposing proximal end of the smart small-bore connector device. The medical device or instrument may include a sensor assembly that provides valuable sensing data with access to a patient's vein, artery, or other biological access, for example. Such data may be representative of one or more environmental characteristics at the access site including, without limitation, a temperature within a body lumen, a blood pressure within the body lumen, a blood glucose level, a sodium level, a potassium level, an indication of pregnancy, a drug concentration level, a white blood cell count, different markers, proteins, and/or chemicals in the patient's blood stream, or any combination thereof.

As described herein, a sensor assembly at the distal end of the smart small-bore connector device includes a sensor or an array of sensors positioned within a vein or an artery to directly contact the patient's blood stream. Each sensor is operatively coupled to the external device using one or more electrical lead wires that are molded in the smart small-bore connector device or coupled to an outside surface or an inside surface of the smart small-bore connector device, for example. In example embodiments, the external device at the proximal end of the smart small-bore connector device is configured with one or more of a variety of electronic and/or communication components to provide power, data transmission, data collection, and/or data analysis capabilities, as well as other capabilities.

In example embodiments, the sensor assembly is configured to sense one or more environmental characteristics within or related to a patient's biological functions including blood or blood stream and generate and transmit one or more signals representative of the one or more environmental characteristics to the external device via the one or more electrical lead wires of the smart small-bore connector device. For example, in example embodiments, the sensor assembly includes one or more sensors, e.g., one sensor or a plurality of sensors. Each sensor of the sensor assembly is configured to measure one or more environmental characteristics, such as described above. Further, the sensor assembly may include one or more particular sensors including, without limitation, a temperature sensor, a sensor that senses a chemical within a patient's blood, a sensor that senses a marker in the patient's blood, a sensor that senses a protein in the patient's blood, or any combination thereof.

In alternative example embodiments, a wire configuration including one or more electrical lead wires may be operatively coupled to the external device to provide suitable communication protocols, e.g., USB level communication having four electrical lead wires, which can enable a wide range of sensors, data rates and/or data types on a well-defined BUS. Other suitable communication protocols include, for example, simple plugin, Wi-Fi, Bluetooth® wireless technology, a universal serial bus connector, Radio Frequency Identification (RFID), Near Field Communication (NCF, a derivative of RFID), and self-contained displays.

Figure 1:
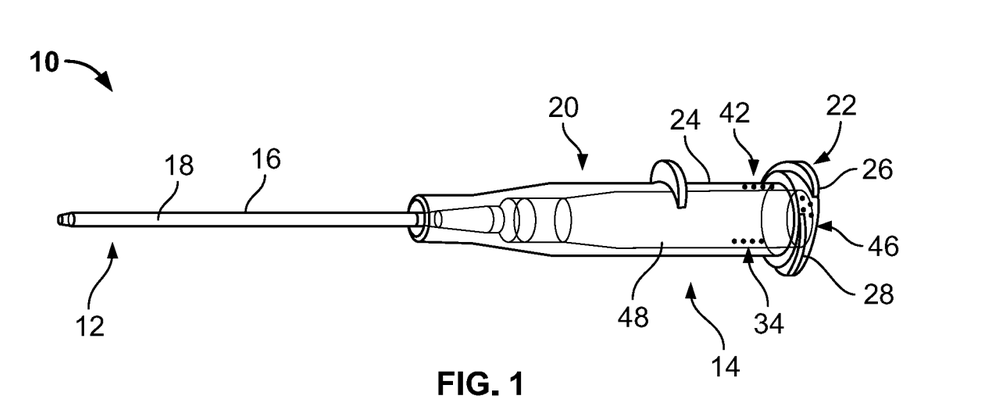
FIGS. 1-3 are perspective side views of example small-bore connector devices with alternative contact points, contact positions, and/or contact locations.
Figure 2:
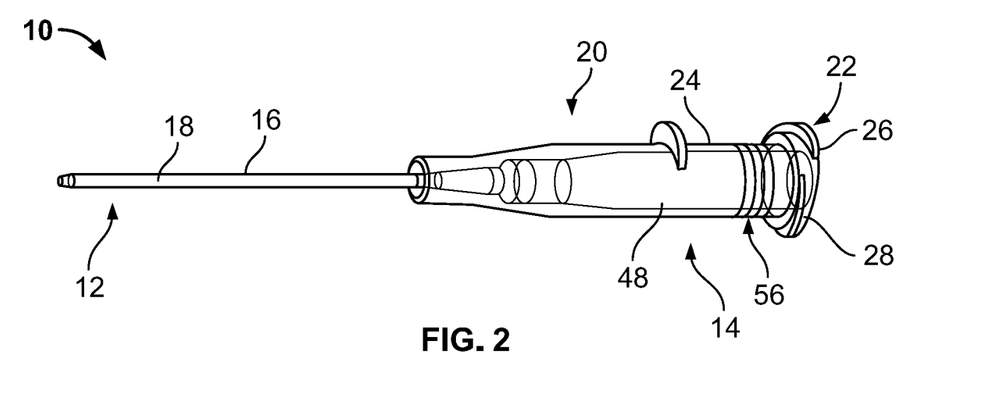
Figure 3:
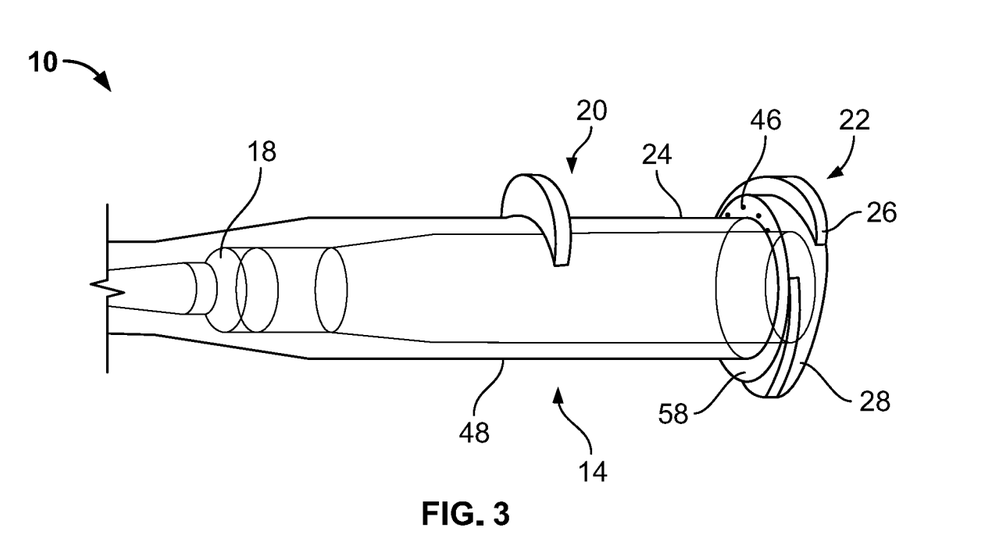

Referring now to the figures, and initially to FIGS. 1-3, an example catheter 10 has a distal end 12 and an opposing proximal end 14. Catheter 10 may include a cannula 16 extending from distal end 12 toward opposing proximal end 14 of catheter 10 in certain example embodiments. Catheter 10 forms or defines a lumen 18 extending between distal end 12 and proximal end 14 of catheter 10. In example embodiments, catheter 10 is configured to couple to a cooperating small-bore fitting or connection, tubing, a hub, or another suitable connection (not shown in FIGS. 1-6) such that lumen 18 provides a fluid flow path through catheter 10. In example embodiments, lumen 18 has a suitable diameter or a suitable cross-sectional dimension to facilitate fluid flow through catheter 10. Additionally or alternatively, lumen 18 may accommodate a medical device or instrument, such as an obturator, for example, that is movably positioned within lumen 18.

At proximal end 14, catheter 10 includes an adapter, such as a small-bore connector 20 shown in FIGS. 1-3, for example. Small-bore connector 20 is configured to removably couple to any suitable medical device or component, for example, a cooperating small-bore fitting, a device, or a medical tubing. The medical device, component, or tubing may include a cooperating element, such as a cooperating small-bore connector, to facilitate coupling the medical device, component, or tubing, for example, to catheter 10. In the example embodiments shown in FIGS. 1-6, small-bore connector 20 is a small-bore connection. In these embodiments, small-bore connector 20 includes a twist-lock mechanism 22 to removably couple small-bore connector 20 to a cooperating small-bore connector having a cooperating twist-lock mechanism. For example, a base 24 of small-bore connector 20 may have one or more external threads 26 formed on a flange 28 of small-bore connector 20 that interlocks with a cooperating internal thread of the cooperating small-bore connector to draw or urge small-bore connector 20 towards the cooperating small-bore connector to maintain a substantially leak-proof coupling between small-bore connector 20 and the cooperating small-bore connector. Small-bore connector 20 can be easily disengaged from the cooperating small-bore connector by rotating small-bore connector 20 in an opposite direction with respect to the cooperating Luer connector to disengage the threads. In alternative example embodiments, small-bore connector 20 may be a slip small-bore fitting that is pressed onto the cooperating small-bore connector.

In example embodiments, small-bore connector 20 includes one or more couplings including, without limitation, one or more electrical couplings, one or more optical couplings, and/one or more resistive couplings. In certain example embodiments, the one or more electrical couplings electrically couple, e.g., in signal communication, electric and/or electronic components on and/or within catheter 10 and/or operatively coupled to catheter 10 to an external device positioned at proximal end 14 of catheter 10 or remotely from catheter 10. The external device may include a delivery device and/or a monitoring device, for example, having one or more microcontrollers or processors. The one or more electrical couplings may provide power from a power source, e.g., a battery, to the electric and/or electronic components of catheter 10. For example, the one or more electrical couplings may electrically couple one or more sensors at distal end 12 of catheter 10 or small-bore connector 20 to the external device at proximal end 14 to transmit data signals and/or command signals between the sensors and the external device.

Referring further to FIGS. 1-6, catheter 10 includes one or more electrical lead wires, e.g., a plurality of electrical lead wires 30, namely, electrical lead wires $30_a$, $30_b$, ..., $30_n$, $30_{n+1}$. Electrical lead wires 30 electrically couple, e.g., in signal communication, electrical components associated with catheter 10 to an external device or component at proximal end 14 of catheter 10, for example. The electrical components may include one or more sensors, an electronic module, circuitry, a microcontroller, and/or a circuit board on catheter 10 or operatively coupled to catheter 10, for example. In example embodiments, one or more sensors are coupled in signal communication to an external device, such as a delivery device and/or a monitoring device, through electrical lead wires 30 to provide sensing capabilities.

Figure 4:
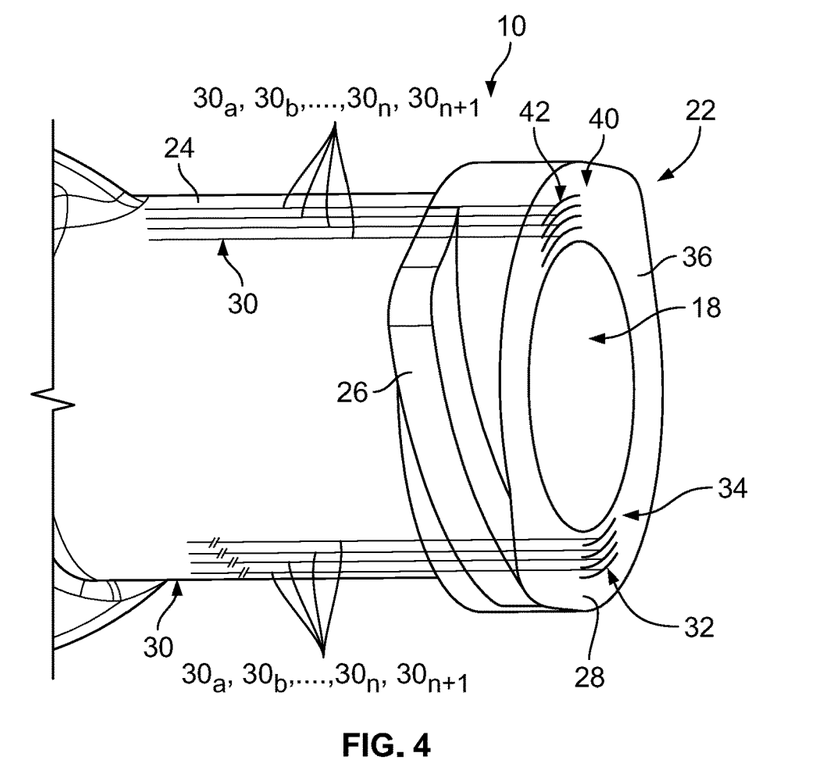
FIGS. 4 and 5 are perspective side views of example small-bore connector devices including insert molded electrical connection elements that terminate on a surface of the small-bore connector device.
Figure 5:
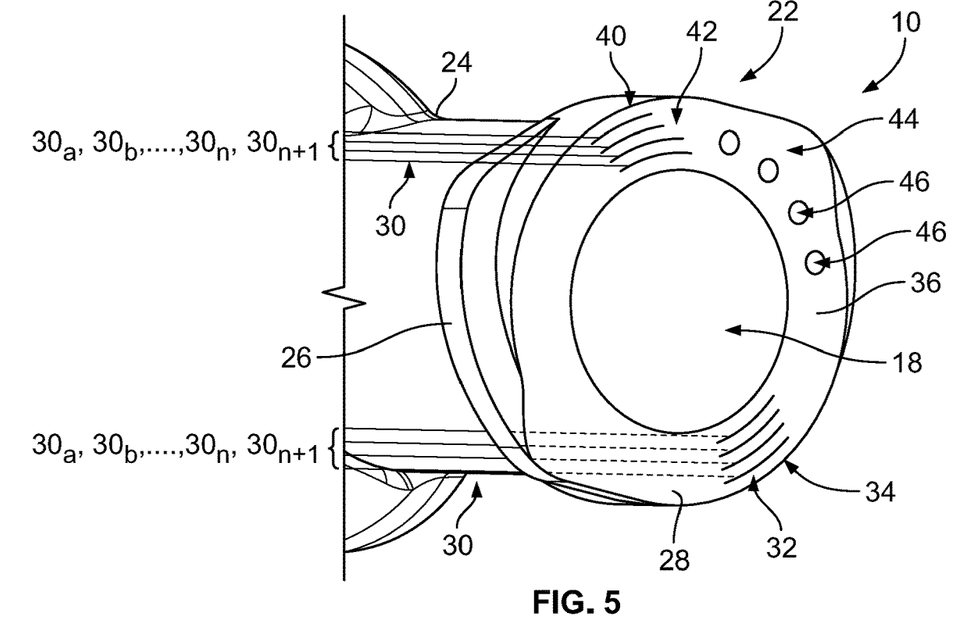

In certain example embodiments, at least a portion of each electrical lead wire 30 is molded onto or molded in catheter 10, for example, molded on or within small-bore connector 20. Each electrical lead wire 30 may extend along a surface of a wall of catheter 10 or may be embedded or molded within at least a portion of a length of the catheter wall between distal end 12 and proximal end 14. As shown in FIGS. 4 and 5, in example embodiments, catheter 10 includes a plurality of electrical lead wires $30_a$, $30_b$, ..., $30_n$, $30_{n+1}$ forming a first array 32 of electrical lead wires 30 arranged in a parallel configuration. Each electrical lead wire 30 is embedded within small-bore connector 20 and terminates at a contact 34 on a proximal surface 36 of flange 28. In certain example embodiments, catheter 10 also includes an additional plurality of electrical lead wires $30_a$, $30_b$, ..., $30_n$, $30_{n+1}$ forming a redundant or second array 40 of electrical lead wires 30 arranged in a parallel configuration and embedded within small-bore connector 20. Each electrical lead wire 30 of second array 40 terminates at a contact point 42 on proximal surface 36 of flange 28. As shown in FIG. 5, in certain example embodiments, catheter 10 may alternatively or in addition to first array 32 and/or second array 40 include a third array 44 of electrical lead wires $30_a$, $30_b$, ..., $30_n$, $30_{n+1}$ arranged in a parallel configuration. Each electrical lead wire 30 of third array 44 is embedded within small-bore connector 20 and terminates at a contact point 46 on proximal surface 36 of flange 28.

Referring again to FIGS. 1-3, contact points 34, 42, and/or 46 can be positioned at any suitable location on catheter 10. For example, as shown in FIG. 1, contact points 34 and/or contact points 42 may be formed through a cylindrical wall 48 of small-bore connector 20, molded into cylindrical wall 48, or formed on an outer surface of cylindrical wall 48. Any suitable number of contact points 34, 42 with corresponding electrical lead wires 30 may be present on or within small-bore connector 20. Contact points 34, 42 may be used to provide power to an electric or electronic component associated with catheter 10 and/or a device operatively coupled to catheter 10, as well as facilitate the transmission of signals between catheter 10 and an external device operatively coupled to catheter 10. Contact points 34, 42 may also be used as a standard USB connection to operatively couple small-bore connector 20 to an external device or a cooperating small-bore connector for another suitable device in certain embodiments. Additionally or alternatively, as described above, one or more contact points, such as contact points 46, may be molded into or formed on a surface of flange 28, e.g., proximal surface 36, or on a surface of one or more external threads 26.

As shown in FIG. 2, one or more contact points may form a coil or cylindrical rings 56 positioned about an outer surface of cylindrical wall 48 to provide contact or interaction with spring fingers on a cooperating small-bore fitting or connection, for example. As shown in FIG. 3, one or more contact points, such as contact points 46, may be molded into or formed on a distally-facing surface 58 of flange 28 providing for a quick connect or snap fit to couple electrical lead wires 30 to the external device.

Figure 6:
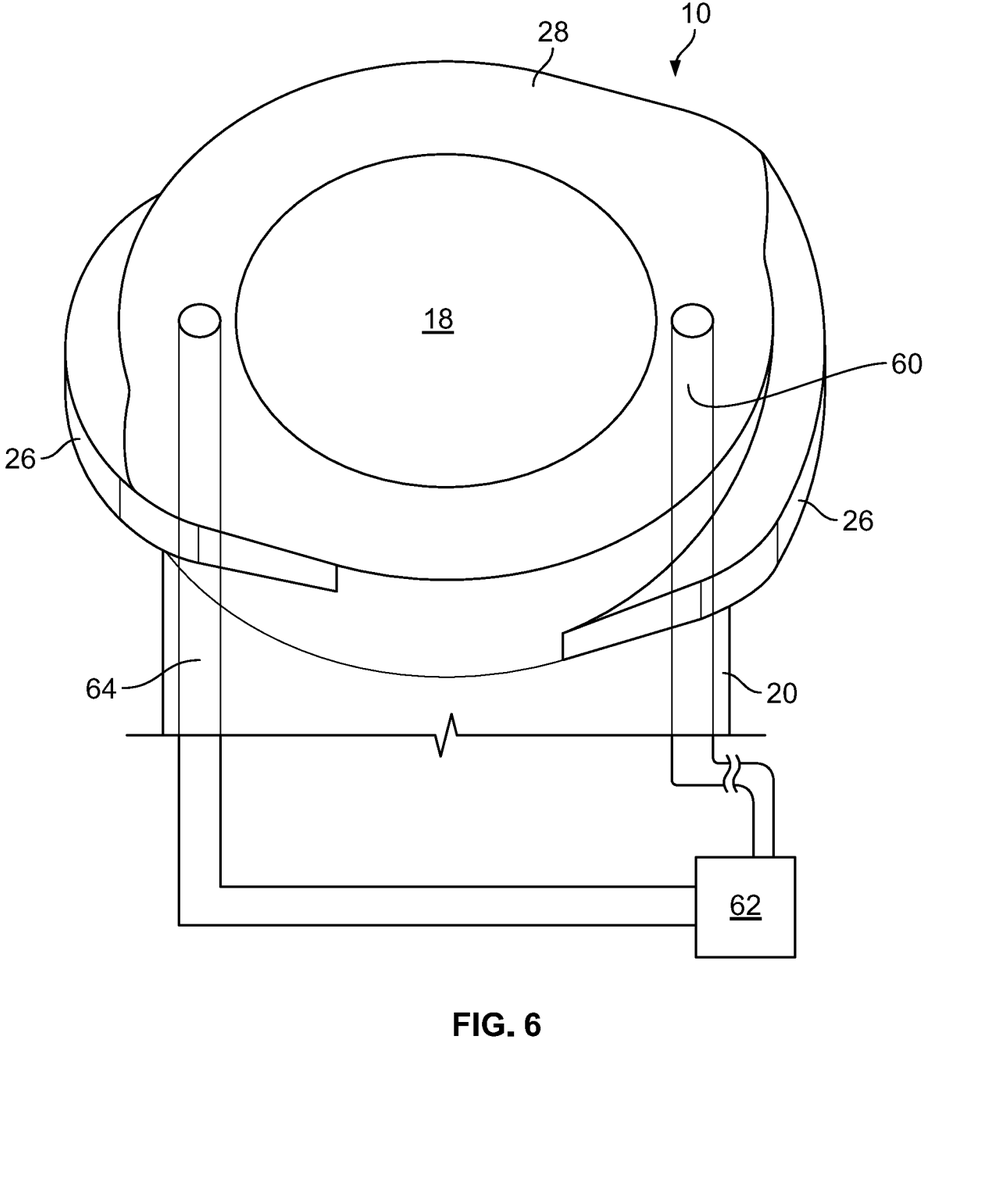
FIG. 6 is a partial perspective side view of an example small-bore connector device including an optical (fiber optic) transmission line insert molded into the small-bore connector device.

In an alternative example embodiment as shown in FIG. 6, one or more suitable optical couplings 60, e.g., one or more optical fibers, can be built in, e.g., molded in, small-bore connector 20 for optical light transmission (fiber optic transmission) between small-bore connector 20 and an external device 62, such as a monitoring device and/or a delivery device. In certain embodiments, this feature is molded in a clear material to provide a fiber optic transmission line or cable without requiring additional parts or components. Additionally or alternatively, one or more data connections 64, similar to a TOS-LINK® style audio transmission cable, can be built in, e.g., molded in, small-bore connector 20 for data transmission between the patient therapy side, e.g., small-bore connector 20, and external device 62. Data connections 64 can be created with more specialized optical fiber cables as needed.

In example embodiments, the external device, e.g., a monitoring device and/or a delivery device, includes one or more processors configured to transmit signals to and receive signals from the sensor assembly. In certain embodiments, a communication module or circuitry operatively coupled to small-bore connector 20 is electrically coupled to, e.g., in signal communication with, the external device for wireless communication with the external device or an external processor. In these embodiments, the communication module or circuitry includes a radio frequency identification transmitter, a near field communication transmitter, a Bluetooth® wireless technology transmitter, a universal serial bus connector, or any suitable combination thereof. The external device may include one or more processors and one or more computer-readable media, one or more communication interfaces, and one or more power sources. The communication interfaces may support both wired and wireless connection to various networks, such as cellular networks, radio, Wi-Fi networks, short range networks (e.g., Bluetooth® technology), and infrared (IR) networks, for example.

Depending on the configuration of the external device, the computer-readable media is an example of computer storage media and may include volatile and nonvolatile memory. Thus, the computer-readable media may include, without limitation, RAM, ROM, EEPROM, flash memory, and/or other memory technology, and/or any other suitable medium that may be used to store computer-readable instructions, programs, applications, media items, and/or data which may be accessed by the external device. The computer-readable media may be used to store any number of functional components that are executable on a processor. The external device may have additional features or functionality. For example, the external device may also include additional data storage devices (removable and/or non-removable). The additional data storage media, which may reside in a control board, may include volatile and nonvolatile, removable and non-removable media implemented in any method or technology for storage of information, such as computer readable instructions, data structures, program modules, or other data. In addition, some or all of the functionality described as residing within the external device may reside remotely from the external device.

Below are several non-limiting, example applications for catheter 10 including small-bore connector 20.

In a first example application, a patient therapy site includes a small blood glucose sensor. An infusing pump is configured to power the sensor through two connections on small-bore connector 20, and send and receive information or data via one or more signals from the sensor to understand how to properly administer a proper amount of insulin or another balancing element.

In a second example application, catheter 10 includes a resistive element in small-bore connector 20 that identifies a size and/or a gauge for the therapy site. A pump or another suitable therapy device is configured to deliver a correct flow rate or a maximum safe flow rate. The resistive value could also indicate a type of device coupled to catheter 10 at small-bore connector 20; thus, facilitating the elimination or decrease in procedures and therapies that might not be compatible with the delivery mechanism.

In example embodiments described herein, a smart small-bore connector device includes a small-bore connector and one or more electrical lead wires in the small-bore connector. The electrical lead wires are configured to provide power to the smart small-bore connector device and/or communication between the smart small-bore connector device and an external or remote device. Each electrical lead wire includes a contact point on a surface of the small-bore connector for electrically coupling the smart small-bore connector device to the external or remote device.

In certain embodiments, the smart small-bore connector device includes one or more electrical wires used for power transmission and/or for data transmission. One or more of the electrical wires may be positioned on a proximal flange of the small-bore connector, on a distal side or surface of the small-bore connector threads, ears and/or flange, and/or on the outer diameter a fluid connection and sealing area of the small-bore connector.

In certain example embodiments, a smart small-bore connector device includes a small-bore connector and at least one optical channel that provides a contact or interface point on a surface of the small-bore connector for optically coupling the smart small-bore connector device to an external or remote device. In certain embodiments, the at least one optical channel may be molded into the mating small-bore connector with a dissimilar material from the small-bore connector material. The optical channel is molded into the mating small-bore connector with a fiber optic cable assembly.

In a third example application, catheter 10 includes an electrical serial number, and, when first used, catheter 10 is configured to communicate with the external device to record a date, a time, and a patient's name, for example. An external database is used to track a therapy time and/or a replacement time, for example. This active identification can then be used to prompt healthcare workers to take appropriate action when alerted, e.g., remove or provide maintenance of catheter 10 or a medical device or instrument operatively coupled to catheter 10.

In a fourth example application, small-bore connector 20 is configured for optical light transmission. In this example application, small-bore connector 20 includes an optical fiber molded into small-bore connector 20 to facilitate communication between catheter 10 and the external device, e.g., a monitoring device and/or a delivery device.

Those of skill in the art will appreciate that embodiments not expressly illustrated herein may be practiced within the scope of the claims, including that features described herein for different embodiments may be combined with each other and/or with currently-known or future-developed technologies while remaining within the scope of the claims. Although specific terms are employed herein, they are used in a generic and descriptive sense only and not for purposes of limitation unless specifically defined by context, usage, or other explicit designation. It is therefore intended that the foregoing detailed description be regarded as illustrative rather than limiting. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment. In the event of any inconsistent disclosure or definition from the present application conflicting with any document incorporated by reference, the disclosure or definition herein shall be deemed to prevail.

What is claimed is:

1. A catheter assembly, comprising:
   a catheter having a distal end and an opposing proximal end, wherein a longitudinal axis extends between the distal end and the proximal end; and
   a connector coupled in fluid communication to the proximal end of the catheter, the connector comprising:
      a base extending along the longitudinal axis and including a flange extending in a perpendicular direction relative to the longitudinal axis, the base comprising a sensor assembly having at least one sensor, the at least one sensor configured to sense one or more environmental characteristics at an access site and generate at least one signal representative of the one or more environmental characteristics; and
      an electrical lead wire operatively coupling the at least one sensor to an external device, wherein the electrical lead wire terminates at a contact point molded into or formed on a distally-facing surface of the flange, wherein the contact point is configured to transmit the at least one signal received from the at least one sensor to the external device.

2. The catheter assembly of claim 1, wherein the one or more environmental characteristics includes a temperature within a body lumen, a blood pressure within the body lumen, a blood glucose level, a sodium level, a potassium level, an indication of pregnancy, a drug concentration level, a white blood cell count, different markers, proteins, and/or chemicals in the patient's blood stream, or any combination thereof.

3. The catheter assembly of claim 1, wherein the electrical lead wire is one of molded in the base or coupled to a surface of the base.

4. The catheter assembly of claim 1, wherein the at least one sensor comprises a temperature sensor, a sensor that senses a chemical within a patient's blood, a sensor that senses a marker in the patient's blood, a sensor that senses a protein in the patient's blood, or any combination thereof.

5. The catheter assembly of claim 1, comprising a plurality of electrical lead wires forming an array of electrical lead wires arranged in a parallel configuration, each electrical lead wire of the array of electrical lead wires embedded within the connector, wherein the contact point is configured to facilitate transmission of signals between the connector and the external device.

6. The catheter assembly of claim 5, further comprising an additional plurality of electrical lead wires forming a second array of electrical lead wires arranged in a parallel configuration and embedded within the connector, each electrical lead wire of the second array of electrical lead wires terminating at a second contact point on the base.

7. The catheter assembly of claim 5, wherein the contact point is formed through a cylindrical wall of the connector, molded into the cylindrical wall, or formed on an outer surface of the cylindrical wall.

8. The catheter assembly of claim 5, wherein the array of electrical lead wires forms a cylindrical ring positioned about an outer surface of a cylindrical wall of the connector.

9. A catheter assembly, comprising:
   a catheter having a distal end and an opposing proximal end, a longitudinal axis extending between the distal end and the proximal end, and a cannula extending along the longitudinal axis from the distal end toward the proximal end;
   a connector coupled in fluid communication with the catheter, the connector configured to provide signal communication between the catheter assembly and an external device, the connector comprising:
      a base extending along the longitudinal axis and having a flange extending in a perpendicular direction relative to the longitudinal axis, the flange forming threads;
      a sensor assembly coupled to the base, the sensor assembly configured to sense one or more environmental characteristics at an access site and generate at least one signal representative of the one or more environmental characteristics; and
      a coupling disposed on a distally-facing surface of the flange, the coupling configured to operatively couple the connector to the external device, the coupling configured to transmit at least one of a data signal and a command signal between the sensor assembly and the external device.

10. The catheter assembly of claim 9, wherein the coupling comprises one of more of the following: an electrical coupling and an optical coupling.

11. The catheter assembly of claim 9, wherein the coupling comprises an electrical lead wire electrically coupling an electrical component of the connector to the external device.

12. The catheter assembly of claim 11, wherein the electrical component comprises one or more of the following: the sensor assembly, an electronic module, circuitry, a microcontroller, or a circuit board.

13. The catheter assembly of claim 11, wherein at least a portion of the electrical lead wire is molded onto or molded in the connector.

14. The catheter assembly of claim 13, wherein the electrical lead wire extends along a surface of a wall of the connector or is embedded within at least a portion of a length of the wall between a distal end and an opposing proximal end of the connector.

15. The catheter assembly of claim 9, wherein the coupling comprises a plurality of electrical lead wires forming an array of electrical lead wires arranged in a parallel configuration, each electrical lead wire of the array of electrical lead wires terminating at a contact point on the base, the contact point configured to facilitate transmission of signals between the sensor assembly and the external device.

16. The catheter assembly of claim 15, further comprising an additional plurality of electrical lead wires forming a second array of electrical lead wires arranged in a parallel configuration, each electrical lead wire of the second array of electrical lead wires terminating at a second contact point on the base, the second contact point configured to facilitate transmission of signals between the sensor assembly and the external device.

17. The catheter assembly of claim 15, wherein the contact point is formed through a cylindrical wall of the connector, molded into the cylindrical wall, or formed on a surface of the cylindrical wall.

18. The catheter assembly of claim 15, wherein the contact point forms a cylindrical ring positioned about an outer surface of a cylindrical wall of the base.

19. The catheter assembly of claim 15, wherein the distally-facing surface of the flange comprises at least one end of the threads.

20. The catheter assembly of claim 9, wherein the coupling comprises an optical coupling in the connector, the optical coupling configured for optical light transmission between the connector and the external device.

* * * * *